United States Patent
van Tol

(10) Patent No.: US 10,690,641 B2
(45) Date of Patent: Jun. 23, 2020

(54) SENSOR CALIBRATION SYSTEMS AND METHODS

(71) Applicant: Trane International Inc., Davidson, NC (US)

(72) Inventor: Joshua van Tol, Winona, MN (US)

(73) Assignee: Trane International Inc., Davidson, NC (US)

( * ) Notice: Subject to any disclaimer, the term of this patent is extended or adjusted under 35 U.S.C. 154(b) by 267 days.

(21) Appl. No.: 15/185,149

(22) Filed: Jun. 17, 2016

(65) Prior Publication Data

US 2016/0370334 A1 Dec. 22, 2016

Related U.S. Application Data

(60) Provisional application No. 62/180,653, filed on Jun. 17, 2015.

(51) Int. Cl.
 *G01C 25/00* (2006.01)
 *G01D 18/00* (2006.01)
 *G01N 33/00* (2006.01)

(52) U.S. Cl.
 CPC ....... *G01N 33/0008* (2013.01); *G01D 18/002* (2013.01)

(58) Field of Classification Search
 CPC . G01D 18/008; G01D 18/002; G01N 33/0008
 USPC ......................................................... 702/104
 See application file for complete search history.

(56) References Cited

U.S. PATENT DOCUMENTS

| | | |
|---|---|---|
| 4,751,648 A | 6/1988 | Sears, III et al. |
| 5,292,280 A | 3/1994 | Janu et al. |
| 5,394,934 A | 3/1995 | Rein et al. |
| 5,950,709 A | 9/1999 | Krueger et al. |
| 6,184,661 B1 | 2/2001 | Becker et al. |
| 6,549,866 B1 | 4/2003 | Bhatnagar |
| 6,711,470 B1 | 3/2004 | Hartenstein et al. |
| 6,892,317 B1 | 5/2005 | Sampath et al. |
| 6,919,809 B2 | 7/2005 | Blunn et al. |
| 7,223,014 B2 * | 5/2007 | Lojen ..................... G01K 15/00 374/120 |
| 7,302,313 B2 | 11/2007 | Sharp et al. |
| 7,341,201 B2 | 3/2008 | Stanimirovic |
| 8,199,005 B2 | 6/2012 | Thomas et al. |
| 8,224,282 B2 | 7/2012 | Songkakul et al. |
| 8,348,840 B2 | 1/2013 | Heit et al. |
| 8,393,169 B2 | 3/2013 | Pham |
| 8,630,741 B1 | 1/2014 | Matsuoka et al. |
| 8,981,950 B1 | 3/2015 | Kates |
| 9,077,183 B2 | 7/2015 | Thomas et al. |

(Continued)

OTHER PUBLICATIONS

Definition of Label, On-line Webster dictionary, printed on Nov. 7, 2018.*

*Primary Examiner* — Michael P Nghiem
(74) *Attorney, Agent, or Firm* — The Salerno Law Firm, P.C.

(57) ABSTRACT

A system for calibrating sensors includes at least one computer server configured to be in communication with at least one uncalibrated sensor and at least one calibrated sensor, and a calibration module stored on the server. The calibration module may be configured to receive calibrated sensor data from the at least one calibrated sensor, and output calibration data to the at least one uncalibrated sensor.

5 Claims, 2 Drawing Sheets

(56) References Cited

U.S. PATENT DOCUMENTS

| | | |
|---|---|---|
| 9,182,751 B1 | 11/2015 | Reeder |
| 2005/0171736 A1 | 8/2005 | Kang |
| 2007/0100666 A1 | 5/2007 | Stivoric et al. |
| 2007/0139208 A1 | 6/2007 | Kates |
| 2008/0086042 A1* | 4/2008 | Brister ............... A61B 5/14532 600/347 |
| 2008/0086273 A1* | 4/2008 | Shults ................ A61B 5/14532 702/19 |
| 2008/0141754 A1 | 6/2008 | Kates |
| 2009/0178459 A1* | 7/2009 | Li ........................ A61B 5/0031 73/1.02 |
| 2010/0298957 A1 | 11/2010 | Sanchez Rocha et al. |
| 2011/0208460 A1* | 8/2011 | Schultz ................ G01D 18/008 702/104 |
| 2012/0215477 A1* | 8/2012 | Tuck ....................... G01P 21/00 702/99 |
| 2013/0181617 A1 | 7/2013 | Maddox |
| 2013/0201316 A1 | 8/2013 | Binder et al. |
| 2014/0203935 A1 | 7/2014 | Kates |
| 2014/0277763 A1 | 9/2014 | Ramachandran et al. |
| 2014/0278144 A1* | 9/2014 | Risk ................... G01N 21/3504 702/24 |
| 2014/0317029 A1 | 10/2014 | Matsuoka et al. |
| 2014/0320295 A1 | 10/2014 | Kates |
| 2015/0006125 A1 | 1/2015 | An et al. |
| 2015/0066404 A1 | 3/2015 | Scelzi |
| 2015/0123654 A1* | 5/2015 | Gagnon ................. G01R 21/08 324/251 |

\* cited by examiner

SENSOR CALIBRATION SYSTEMS AND METHODS

CROSS-REFERENCE TO RELATED APPLICATION

This application claims the benefit of and priority to U.S. Provisional Application Ser. No. 62/180,653 entitled "SENSOR CALIBRATION SYSTEMS AND METHODS" and filed Jun. 17, 2015, the entirety of which is hereby incorporated by reference herein for all purposes.

BACKGROUND

1. Technical Field

The present disclosure is directed to systems, apparatus, and methods for improving calibration systems, more particularly, calibration systems for $CO_2$ sensors used in HVAC installations.

2. Background of Related Art

Heating, ventilation, and air conditioning systems (HVAC systems) typically utilize one or more sensors, thermostats, and/or HVAC controllers to monitor environmental conditions in a building and to operate HVAC equipment installed at the building. Traditional systems utilize components which are interconnected using traditional hard-wiring techniques using electrical conductors routed within the physical structure. Hard-wired systems are generally reliable, but the costs of cabling and installation are high. This is particularly true when installing devices in existing structures where cabling must be snaked through walls and ceilings. More recently, the use of wireless HVAC devices has become popular because they are cost-effective and easy to install.

Some types of sensors used in HVAC systems, e.g., $CO_2$ sensors, require periodic access to a background level reading in order to reset their baseline. For example, traditional $CO_2$ sensors may require calibration after certain intervals of time to reset the background reference by taking a reading of ambient atmosphere at a time when there are no sources of $CO_2$ (e.g., people) in a particular location. However, in buildings that are constantly occupied, or in places where access to an ambient reading is otherwise difficult, traditional $CO_2$ sensors must be manually recalibrated (e.g., by removal and/or supplying the sensor with a suitable calibration gas). This may be time consuming and difficult, especially where sensor devices are located in hard to reach locations. A solution to the above problem would be a welcome advance in the art.

SUMMARY

In accordance with at least one aspect of this disclosure, a system for calibrating sensors includes at least one computer server configured to be in communication with at least one uncalibrated sensor and at least one calibrated sensor, and a calibration module stored on the server. The calibration module is configured to receive calibrated sensor data from the at least one calibrated sensor, and output calibration data to the at least one uncalibrated sensor.

In accordance with at least one aspect of this disclosure, the calibration module may include an aging model configured to output the calibration data.

In accordance with at least one aspect of this disclosure, the calibration module may be configured to extract calibration coefficients from the calibrated sensor data.

In accordance with at least one aspect of this disclosure, the calibration module may be configured to input the calibration coefficients into the aging model.

In accordance with at least one aspect of this disclosure, the calibration module may be configured to receive uncalibrated sensor data from the at least one uncalibrated sensor.

In accordance with at least one aspect of this disclosure, the calibration module may be configured to create the aging model based on the calibrated sensor data.

In accordance with at least one aspect of this disclosure, the calibration module may be configured to input the uncalibrated sensor data into the aging model.

In accordance with at least one aspect of this disclosure, the at least one calibrated sensor may be a population of calibrated sensors.

In accordance with at least one aspect of this disclosure, the calibrated sensor data may include at least one of time since last calibration, age of the sensor, one or more environmental conditions, or location from each calibrated sensor.

In accordance with at least one aspect of this disclosure, the at least one uncalibrated sensor may be a population of uncalibrated sensors.

In accordance with at least one aspect of this disclosure, the calibration module may be configured to output unique calibration data for each uncalibrated sensor based on the uncalibrated sensor data from each uncalibrated sensor.

In accordance with at least one aspect of this disclosure, the uncalibrated sensor data may include at least one of time since last calibration, age of the sensor, one or more environmental conditions, or location from each uncalibrated sensor.

In accordance with at least one aspect of this disclosure, a sensor for an HVAC system includes a processor, a memory, and an auto-calibration module stored in the memory and configured to be executed by the processor. The auto-calibration module is configured to determine if the sensor may be locally auto-calibrated based on local conditions and to locally auto-calibrate the sensor against a reliable baseline reading if it is determined that the sensor may be locally auto-calibrated. The auto-calibration module may also be configured to receive calibration data from a calibration module of a remote server if it is determined that the sensor cannot be auto-calibrated based on the local conditions.

In accordance with at least one aspect of this disclosure, the auto-calibration module may be configured to output uncalibrated sensor data to the calibration module.

In accordance with at least one aspect of this disclosure, the auto-calibration module may be configured to output calibrated sensor data to the calibration module if the sensor is locally auto-calibrated.

In accordance with at least one aspect of this disclosure, the local conditions may include at least one of local environment conditions, location data of the sensor, an input indication that the sensor cannot be auto-calibrated, a building schedule at a required interval of calibration, or a variance of a current attempted baseline reading versus a previous known baseline reading.

In accordance with at least one aspect of this disclosure, a method for calibrating an uncalibrated sensor may include receiving calibrated sensor data from a population of calibrated sensors, and outputting calibration data to the uncalibrated sensor to calibrate the uncalibrated sensor.

In accordance with at least one aspect of this disclosure, the method may further include inputting the calibrated sensor data into an aging model.

In accordance with at least one aspect of this disclosure, the method may further include creating the aging model based on the calibrated sensor data.

In accordance with at least one aspect of this disclosure, the method may further include receiving uncalibrated sensor data and inputting the uncalibrated sensor data into the aging model to output the calibration data.

BRIEF DESCRIPTION OF THE DRAWINGS

Various embodiments of the disclosed system and method are described herein with reference to the drawings wherein.

Figure 1:
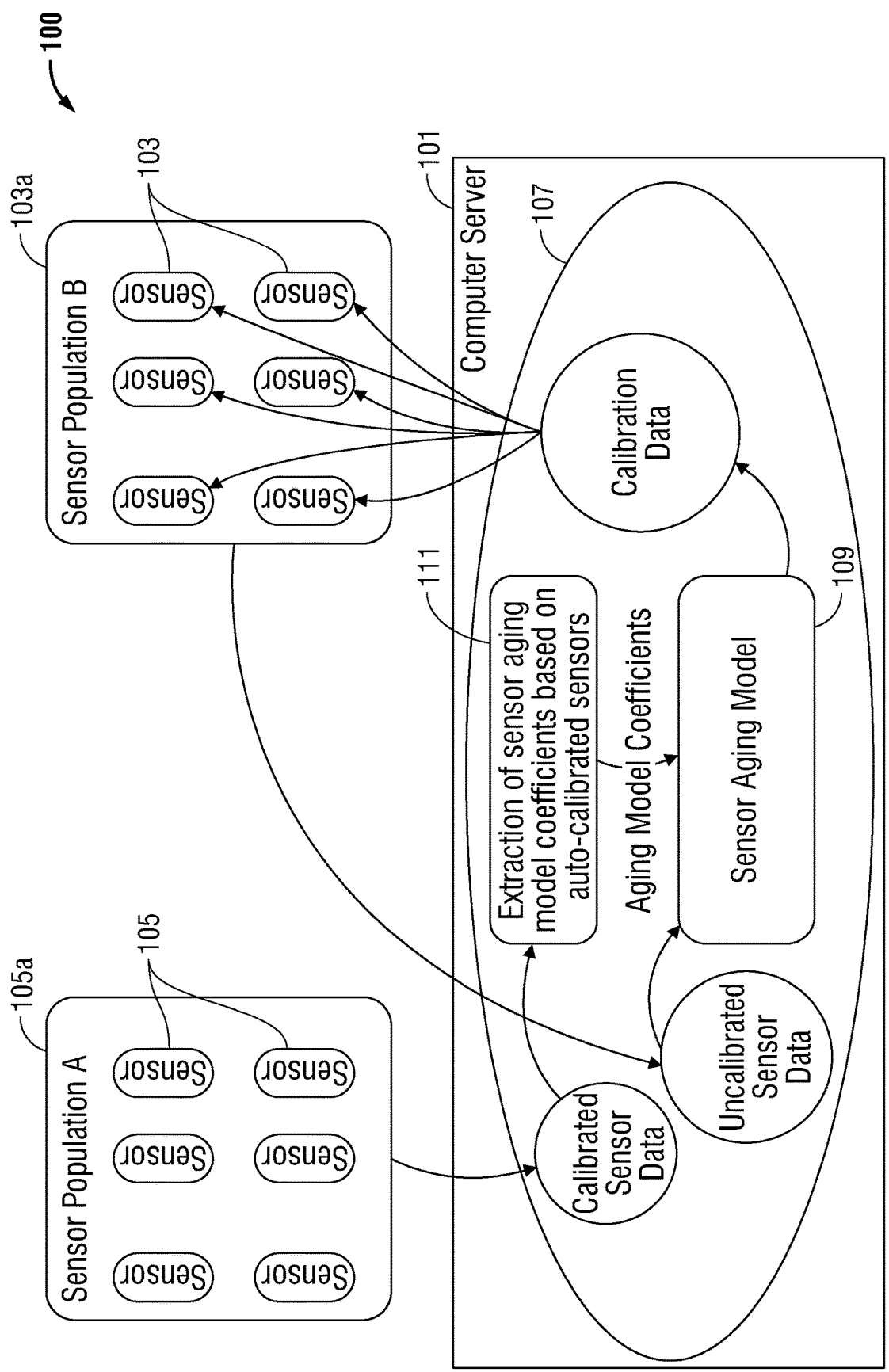
FIG. 1 is schematic diagram of an embodiment of a system in accordance with the present disclosure, showing input and output data into subroutines of an embodiment of a calibration module.

The various aspects of the present disclosure mentioned above are described in further detail with reference to the aforementioned figures and the following detailed description of exemplary embodiments.

DETAILED DESCRIPTION

Particular illustrative embodiments of the present disclosure are described hereinbelow with reference to the accompanying drawings; however, the disclosed embodiments are merely examples of the disclosure, which may be embodied in various forms. Well-known functions or constructions and repetitive matter are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements which may perform the same, similar, or equivalent functions. The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

The present disclosure is described herein in terms of functional block components and various processing steps. It should be appreciated that such functional blocks and/or processing steps may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices.

Similarly, software elements of the present disclosure may be implemented with any programming or scripting language such as C, C++, C#, Java, COBOL, assembler, PERL, Python, PHP, or the like, with the various algorithms being implemented with any combination of data structures, objects, processes, routines or other programming elements. The object code created may be executed by any device, on a variety of operating systems, including without limitation RTOS, Apple OSX®, Apple iOS®, Google Android®, HP WebOS®, Linux, UNIX®, Microsoft Windows®, and/or Microsoft Windows Mobile®.

It should be appreciated that the particular implementations described herein are illustrative of the disclosure and its best mode and are not intended to otherwise limit the scope of the present disclosure in any way. Examples are presented herein which may include data items which are intended as examples and are not to be construed as limiting. Indeed, for the sake of brevity, conventional data networking, application development and other functional aspects of the systems (and components of the individual operating components of the systems) may not be described in detail herein. It should be noted that many alternative or additional functional relationships or physical or virtual connections may be present in a practical electronic system or apparatus. In the discussion contained herein, the terms user interface element and/or button are understood to be non-limiting, and include other user interface elements such as, without limitation, pushbutton, a proximity sensor, a hyperlink, clickable image, and the like.

As will be appreciated by one of ordinary skill in the art, aspects of the present disclosure may be embodied as a method, a data processing system, a device for data processing, and/or a computer program product. Certain aspects of the present disclosure may take the form of a computer program product on a computer-readable storage medium having computer-readable program code means embodied in the storage medium. Any suitable computer-readable storage medium may be utilized, including hard disks, CD-ROM, DVD-ROM, optical storage devices, magnetic storage devices, semiconductor storage devices (e.g., EEPROM, mask ROM, flash memory, USB thumb drives) and/or the like.

Computer program instructions embodying certain aspects of the present disclosure may also be stored in a computer-readable memory that may direct a computer or other programmable data processing apparatus to function in a particular manner, such that the instructions stored in the computer-readable memory produce an article of manufacture, including instruction means, that implement the function specified in the description or flowchart block(s). The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the present disclosure.

One skilled in the art will also appreciate that, for security and/or any other suitable reason, any components, data structures, and communications links may include any of various suitable security features, such as firewalls, access codes, encryption, de-encryption, compression, decompression, and/or the like. In some instances, the steps recited herein may be executed in any order and are not limited to the order presented.

Exemplary embodiments are disclosed herein which operate in accordance with the ZigBee® wireless mesh networking standards, however, it should be understood that embodiments of the present disclosure are applicable to any wired or wireless network architecture, including without limitation Z-Wave®, in which the features and advantages discussed herein may be advantageously employed.

Referring to FIG. 1, in accordance with the present disclosure, a system 100 for calibrating sensors may include at least one computer server 101 configured to be in communication with one or more uncalibrated sensors 103 (e.g., sensor population 103a) and one or more calibrated sensors 105 (e.g., sensor population 105a). A calibration module 107 is included in the at least one server 101 and is configured to receive calibrated sensor data from one or more of the calibrated sensors 105 individually and/or calibrated sensor data from the population 105a as a whole. The calibration module 107 may also output calibration data to one or more of the uncalibrated sensors 103.

The calibration module 107 may be embodied as any suitable software and/or hardware as is appreciated by those having skill in the art and/or as described herein. For example, while shown as existing on a single server 101, all or portions of the calibration module 107 may be stored and/or operated on any suitable number of servers (e.g., the cloud).

The calibration module 107 may include an aging model 109 configured to calculate and/or output the calibration data. The calibration module 107 may be configured to create the aging model 109 based on the calibrated sensor data. However, it is contemplated that the aging model 109 may be manually input to the calibration module 109 or may be created in any other suitable manner.

The calibrated sensor data may include at least one of a time since last calibration, age of the sensor, one or more environmental conditions (e.g., temperature, pressure, average $CO_2$ values, baseline $CO_2$ values), and/or location from each calibrated sensor. Any other suitable sensor data from the calibrated sensors 105 is contemplated herein.

In certain embodiments, the calibration module 107 may be configured to extract calibration coefficients from the calibrated sensor data (e.g., via extraction subroutine 111). In such embodiments, the calibration module 107 is configured to input the calibration coefficients into the aging model 109.

The calibration module 107 may be configured to receive uncalibrated sensor data from the at least one uncalibrated sensor 103 (e.g., to input into the complete aging model 109 in order to output sensor specific calibration data). The uncalibrated sensor data may include at least one of a time since last calibration, age of the sensor, one or more environmental conditions (e.g., temperature, pressure, average $CO_2$ values, baseline $CO_2$ values), and/or a location (e.g., a geographic location, a type of location such as an office, gymnasium, or bathroom) from each calibrated sensor. Any other suitable sensor data (e.g., local weather data such as average background $CO_2$, particulate counts, volatile organic compound readings, outside air temperature, humidity, etc.) from the uncalibrated sensors is contemplated herein.

In a non-limiting example, the aging model 109 is a function of two variable sets, the first being calibration coefficients and the second being uncalibrated sensor data. As such, by inputting known calibration coefficients from the calibrated sensors 105, as well as suitable uncalibrated sensor data, the aging model 109 may output a suitable formula, model, coefficients, or other suitable calibration data to one or more of the uncalibrated sensors 103 such that the uncalibrated sensors 103 may utilize the calibration data to auto-calibrate without an accurate baseline reading. As such, the aging model may characterize the aging related calibration drift of the uncalibrated sensors 103.

In certain embodiments, the calibration module 107 may be configured to output unique calibration data for each uncalibrated sensor 103 based on the uncalibrated sensor data from each uncalibrated sensor 103. For example, an uncalibrated sensor 103 that has not been calibrated in several months may have different calibration data than an uncalibrated sensor 103 that was last calibrated more recently, e.g., as a function of the aging model 109. As another example, the output calibration data may be a function of average temperature, average pressure, average humidity, or any other suitable environmental condition to which each uncalibrated sensor 103 is exposed over a sampling period (e.g., time since last calibration, a predetermined number of samples taken, a predetermined sampling interval, time since manufacture).

Figure 2:
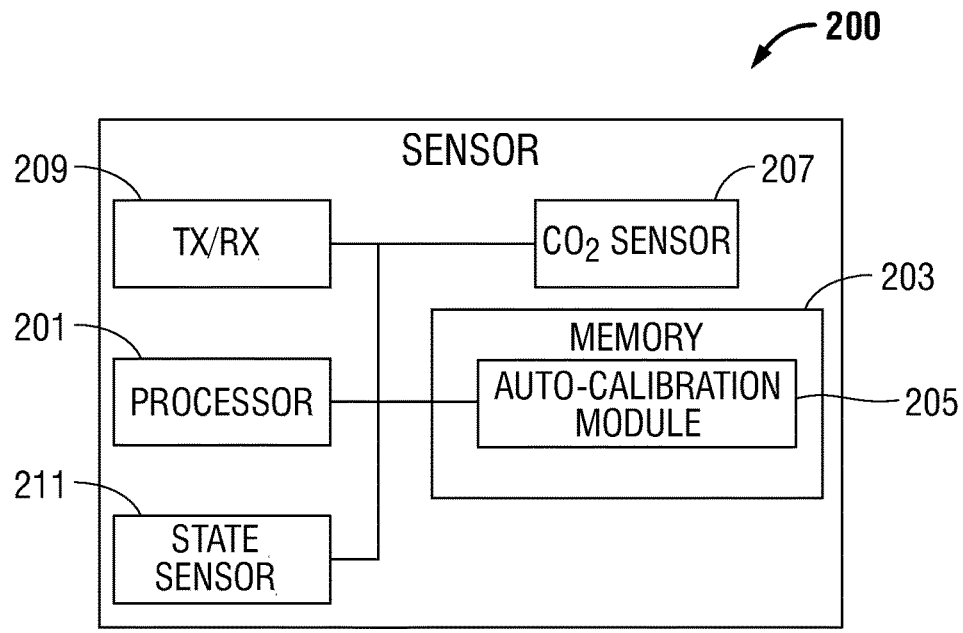
FIG. 2 is a schematic diagram of an embodiment of a sensor in accordance with this disclosure.

Referring additionally to FIG. 2, a sensor 200 for an HVAC system (e.g., a CO2 sensor) may include a processor 201, a memory 203, and an auto-calibration module 205 stored in the memory 203 that is configured to be executed by the processor 201. For example, the auto-calibration module 205 may include any suitable logic hardware and/or software to execute an auto-calibration routine. For example, the auto-calibration module 205 may be configured to determine if the sensor 200 may be locally auto-calibrated based on local conditions (e.g., average CO2 over a predetermined period of time, location). For example, the auto-calibration module 205 may determine if a reliable baseline reading is available to calibrate against (e.g., if the CO2 sensor 207 will be exposed to clean ambient air at any point before required calibration).

The sensor 200 may be configured to locally auto-calibrate the sensor 200 against a reliable baseline reading if it is determined that the sensor 200 may be locally auto-calibrated. In the case where it is determined that the sensor 200 cannot be auto-calibrated based on the local conditions, the auto-calibration module 205 may also be configured to receive calibration data (e.g., through transmitter/receiver (TX/RX) 209) from a calibration module 107 of a remote server 101.

The auto-calibration module 205 may be configured to output uncalibrated sensor data to the calibration module 107. For example, sensor 200 may include state sensor 211 for sensing one or more suitable conditions of the sensor 200 or environment around the sensor 200 (e.g., temperature, pressure, age, time since last calibration) in addition to the primary sensor (e.g., $CO_2$ sensor). The auto-calibration module 205 may then output the calibration data to the calibration module 107 on the remote server 101 via the TX/RX 209. The auto-calibration module 205 may additionally or alternatively send a request for calibration data to the server 101 in order to notify the calibration module 107 that the sensor 200 is an uncalibrated sensor 103 as described above.

In the case where the sensor 200 may be auto-calibrated, the auto-calibration module 205 may be configured to output calibrated sensor data to the calibration module 107 (e.g., to act as a calibrated sensor 105 as described above) via TX/RX 209. This calibrated sensor data may be used as described above to create calibration data for other uncalibrated sensors 103 that cannot be auto-calibrated as described above.

Certain embodiments of the local conditions used to determine if the sensor 200 may auto-calibrate may include at least one of local environment conditions (e.g., temperature, pressure, humidity, chemical content of air). In certain embodiments, the local conditions may include location data of the sensor (e.g., the type of building the sensor is located in, occupation percentage/time/schedule of the building, a specific location of the sensor 200 within the building and the like).

In certain embodiments, the local conditions may include a variance of a current attempted baseline reading versus a previous known baseline reading. For example, if a $CO_2$ reading of a current attempted baseline reading are an order of magnitude different than the previous known baseline reading, the auto-calibration module 205 may determine that the baseline reading is unreliable. The sensor 200 may try again at a predetermined interval or may request calibration data from the calibration module 107 of the remote server 101.

Figure 3:
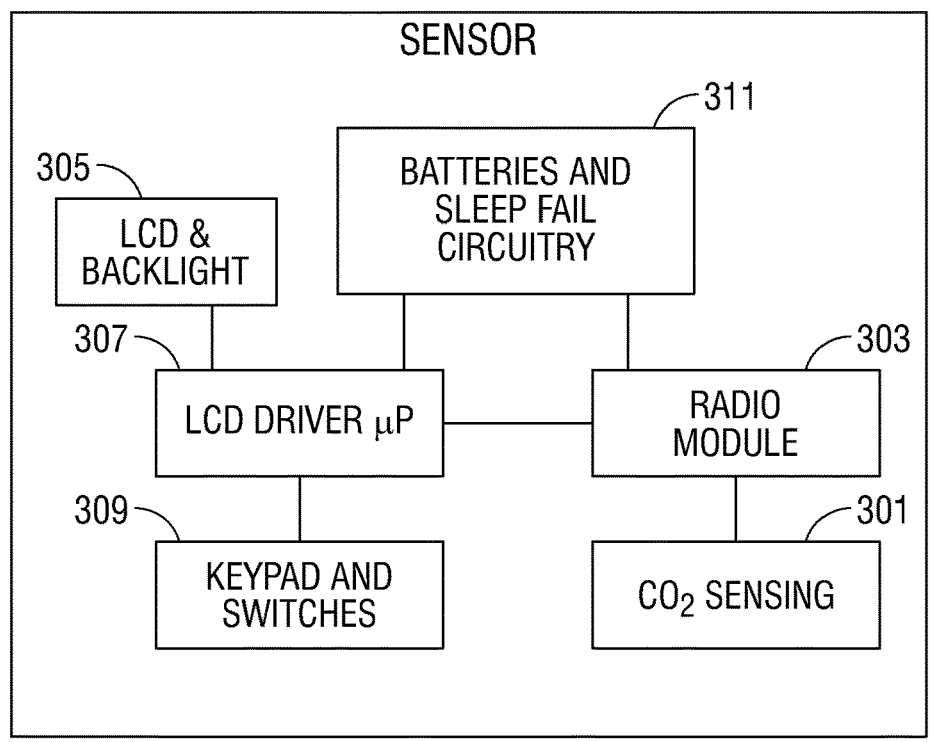
FIG. 3 is a schematic diagram of an embodiment of a sensor in accordance with this disclosure.

Referring to FIG. 3, an embodiment of a sensor device 300 for an HVAC system is shown. The sensor 300 includes a $CO_2$ sensor 301 and a radio module 303 that is connected to the $CO_2$ sensor 301. The $CO_2$ sensor 301 can include any suitable portions or all of sensor 200 as described above (e.g., auto-calibration module 205), and/or any other suitable features. For example, the sensor device 300 may include and LCD display 305 (e.g., including a backlight) operatively connected to an LCD driver 307 to display images (e.g., numbers, letters) on the LCD display 305. The sensor device 300 can also include a keypad and/or one or more switches 309 which allow a user to input commands into the sensor device 300. The sensor device 300 can also include one or more batteries 311 as well as other suitable circuitry (e.g., sleep fail circuitry to prevent a sleep mode failure).

In certain embodiments, an input indication that the sensor 301 cannot be auto-calibrated may be programmed and/or manually switched by a user before or after placing the sensor 301. For example, if a user knows that the location or intended use of a particular sensor 301 will prevent a reliable baseline reading, then the user may operate a suitable control (e.g., the keypad and/or switches 309, a touch screen display, a digital command from a remote device) to instruct the auto-calibration module 205 to operate assuming it cannot be auto-calibrated without calibration data from the server 101.

Certain embodiments may also allow for tandem calibration (e.g., use of calibration data and baseline readings) to keep the sensor 301 calibrated within a desired accuracy range (e.g. within a confidence interval) for as long as possible. If the accuracy of the sensor 301 is determined to be outside of a predetermined range, the sensor 301 may notify an operator (e.g., via any suitable data communication, via LCD display 305) to manually recalibrate.

In accordance with at least one aspect of this disclosure, a method for calibrating an uncalibrated sensor may include receiving calibrated sensor data from a population of calibrated sensors, and outputting calibration data to the uncalibrated sensor to calibrate the uncalibrated sensor. The method may further include creating the aging model based on the calibrated sensor data. The method may further include inputting the calibrated sensor data into an aging model. In certain embodiments, the method may further include receiving uncalibrated sensor data and inputting the uncalibrated sensor data into the aging model to output the calibration data.

As is appreciated by those skilled in the art, the method may be executed via any suitable hardware and/or software as described herein above. While embodiments of sensors as described above are shown as wireless, it is contemplated that one or more of the sensors can be wired sensors.

$CO_2$ sensors as described hereinabove may be used in spaces that are occupied all the time (e.g., hospitals, prisons) and may still be calibrated without manual calibration by using calibration data from the system 100. Also, certain embodiments of sensor 200 as described above may determine if it is a calibrated sensor with access to local calibration or if it is an uncalibrated sensor that cannot auto-calibrate without calibration data. This allows manufacture and use of a single type of sensor (e.g., wireless or wired) that may form both data providers and data users of the system 100. Such systems, apparatuses and methods as described herein may eliminate the need for constant over-ventilation which is expensive and wasteful. While the sensors as described herein are directed to HVAC sensors such as $CO_2$ sensors, it is contemplated that any suitable sensor could be utilized with the herein described systems and methods.

While the calibration module 107 is described as including the aging model 109 on the one or more servers 101, it is contemplated that the aging model 109 may be included with one or more of the sensors 200 such that calibrated sensor data may be directly input into each uncalibrated sensor 103. This may reduce the complexity of the server/cloud base algorithms and allow for sensor-to-sensor connection for remote calibration. In such a case, sensor selection and placement for a population of sensors 103a, 105a may be such that a plurality of sensors may receive calibration data based on one or more sensors that are known to be able to calibrate (e.g., especially where all sensors age in a similar manner).

Aspects

It is noted that any of aspects described below may be combined with each other in any suitable combination as is appreciated by those having ordinary skill in the art.

Aspect 1. A system for calibrating sensors may include at least one computer server configured to be in communication with at least one uncalibrated sensor and at least one calibrated sensor, and a calibration module stored on the server. The calibration module may be configured to receive calibrated sensor data from the at least one calibrated sensor, and output calibration data to the at least one uncalibrated sensor.

Aspect 2. The calibration module may include an aging model configured to output the calibration data.

Aspect 3. The calibration module may be configured to extract calibration coefficients from the calibrated sensor data.

Aspect 4. The calibration module may be configured to input the calibration coefficients into the aging model.

Aspect 5. The calibration module may be configured to receive uncalibrated sensor data from the at least one uncalibrated sensor.

Aspect 6. The calibration module may be configured to create the aging model based on the calibrated sensor data.

Aspect 7. The calibration module may be configured to input the uncalibrated sensor data into the aging model.

Aspect 8. The at least one calibrated sensor may be a population of calibrated sensors.

Aspect 9. The calibrated sensor data may include at least one of time since last calibration, age of the sensor, one or more environmental conditions, or location from each calibrated sensor.

Aspect 10. The at least one uncalibrated sensor may be a population of uncalibrated sensors.

Aspect 11. The calibration module may be configured to output unique calibration data for each uncalibrated sensor based on the uncalibrated sensor data from each uncalibrated sensor.

Aspect 12. The uncalibrated sensor data may include at least one of a time since last calibration, age of the sensor, one or more environmental conditions, or a location of each uncalibrated sensor.

Aspect 13. A sensor for an HVAC system may include a processor, a memory, and an auto-calibration module stored in the memory and configured to be executed by the processor. The auto-calibration module may be configured to determine if the sensor may be locally auto-calibrated based on local conditions and to locally auto-calibrate the sensor against a reliable baseline reading if it is determined that the sensor may be locally auto-calibrated. The auto-calibration module may also be configured to receive calibration data from a calibration module of a remote server if it is determined that the sensor cannot be auto-calibrated based on the local conditions.

Aspect 14. The auto-calibration module may be configured to output uncalibrated sensor data to the calibration module.

Aspect 15. The auto-calibration module may be configured to output calibrated sensor data to the calibration module if the sensor is locally auto-calibrated.

Aspect 16. The local conditions may include at least one of local environment conditions, location data of the sensor, an input indication that the sensor cannot be auto-calibrated, a building schedule at a required interval of calibration, or a variance of a current attempted baseline reading versus a previous known baseline reading.

Aspect 17. A method for calibrating an uncalibrated sensor may include receiving calibrated sensor data from a population of calibrated sensors, and outputting calibration data to the uncalibrated sensor to calibrate the uncalibrated sensor.

Aspect 18. The method may further include inputting the calibrated sensor data into an aging model.

Aspect 19. The method may further include creating the aging model based on the calibrated sensor data.

Aspect 20. The method may further include receiving uncalibrated sensor data and inputting the uncalibrated sensor data into the aging model to output the calibration data.

Particular embodiments of the present disclosure have been described herein, however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in any appropriately detailed structure.

What is claimed is:

1. A sensor for an HVAC system, comprising:
    a processor;
    a memory; and
    a set of instructions stored in the memory and executable on the processor, which, when executed by the processor, cause the sensor to:
    determine if the sensor may be locally auto-calibrated based on local conditions;
    locally auto-calibrate the sensor against a reliable baseline reading upon a determination that the sensor may be locally auto-calibrated based on the local conditions;
    output uncalibrated sensor data to a calibration module, upon a determination that the sensor cannot be auto-calibrated based on the local conditions, to populate an uncalibrated sensor dataset of the calibration module; and
    receive calibration data, based on the uncalibrated sensor data, from the calibration module of a remote server, to calibrate the sensor.

2. The sensor of claim 1, further including instructions stored in the memory and executable on the processor, which, when executed by the processor, cause the sensor to output calibrated sensor data to the calibration module if the sensor is locally auto-calibrated to populate a calibrated sensor dataset of the calibration module.

3. The sensor of claim 1, wherein the local conditions include at least one of local environment conditions, location data of the sensor, an input indication that the sensor cannot be auto-calibrated, a building schedule at a required interval of calibration, or a variance of a current attempted baseline reading versus a previous known baseline reading.

4. A sensor for an HVAC system, comprising:
    a processor;
    a memory; and
    a set of instructions stored in the memory and executable on the processor, which, when executed by the processor, cause the sensor to:
    determine if the sensor may be locally auto-calibrated based on local conditions;
    locally auto-calibrate the sensor against a reliable baseline reading upon a determination that the sensor may be locally auto-calibrated based on the local conditions;
    receive calibration data to calibrate the sensor from a calibration module of a remote server upon a determination that the sensor cannot be auto-calibrated based on the local conditions; and
    output calibrated sensor data to the calibration module if the sensor is locally auto-calibrated to populate a calibrated sensor dataset of the calibration module.

5. The sensor of claim 4, wherein the local conditions include at least one of local environment conditions, location data of the sensor, an input indication that the sensor cannot be auto-calibrated, a building schedule at a required interval of calibration, or a variance of a current attempted baseline reading versus a previous known baseline reading.

* * * * *